(12) United States Patent
Ein-Gal

(10) Patent No.: US 7,048,699 B2
(45) Date of Patent: *May 23, 2006

(54) NON-CYLINDRICAL ACOUSTIC WAVE DEVICE

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/949,885

(22) Filed: Sep. 12, 2001

(65) Prior Publication Data

US 2003/0050559 A1 Mar. 13, 2003

(51) Int. Cl.
A61B 17/22 (2006.01)

(52) U.S. Cl. .................... 601/2; 601/4; 600/439

(58) Field of Classification Search ........... 601/2–4; 600/459, 472, 439; 367/73, 140; 73/625, 73/629, 632, 633, 634, 627
See application file for complete search history.

(56) References Cited

U.S. PATENT DOCUMENTS

| | | | | |
|---|---|---|---|---|
| 3,451,260 A | * | 6/1969 | Thurstone | 73/614 |
| 3,942,531 A | | 3/1976 | Hoff et al. | |
| 4,025,805 A | * | 5/1977 | Coltman et al. | 310/335 |
| 4,248,090 A | * | 2/1981 | Glenn | 600/472 |
| 4,539,989 A | | 9/1985 | Forssman et al. | |
| 4,664,111 A | * | 5/1987 | Reichenberger | 601/4 |
| 4,674,505 A | | 6/1987 | Pauli et al. | |
| 4,844,081 A | * | 7/1989 | Northeved et al. | 600/439 |
| 5,058,569 A | | 10/1991 | Hassler et al. | |
| 5,174,280 A | * | 12/1992 | Gruenwald et al. | 601/4 |

* cited by examiner

Primary Examiner—Eleni Mantis Mercader
(74) Attorney, Agent, or Firm—Dekel Patent Ltd.; David Klein

(57) ABSTRACT

An acoustic wave device including a non-cylindrical and non-point acoustic wave transducer adapted to generate an acoustic wave and positioned along a longitudinal axis, and a reflector arranged with respect to the transducer so as to focus an acoustic wave emanating from the transducer to a focal point.

8 Claims, 2 Drawing Sheets

NON-CYLINDRICAL ACOUSTIC WAVE DEVICE

FIELD OF THE INVENTION

The present invention relates to generation and focusing of acoustic waves in general, and particularly to a non-cylindrical acoustic wave source device, useful in medical treatments, such as extracorporeal shockwave treatment (ESWT).

BACKGROUND OF THE INVENTION

Generation and focusing of acoustic waves (or shock-waves, the terms being used interchangeably throughout) for purposes of medical treatment such as stone fragmentation or orthopedic treatment are accomplished through a variety of methods. Each method incorporates acoustic wave generation and associated focusing apparatus. The prior art may be classified according to the geometry of the acoustic wave generation and associated focusing: point source and ellipsoidal reflector, planar source and acoustic lens, cylindrical source and parabolic reflector, and spherical source with no additional focusing. The prior art typically converts electrical energy into acoustic waves, such as by generating a strong pulse of an electric or magnetic field, usually by a capacitor discharge, and then converting the electromagnetic field into acoustic energy.

Point sources for the generation of acoustic waves in a lithotripter are described in various patents, such as U.S. Pat. Nos. 3,942,531 and 4,539,989, for example, the disclosures of which are incorporated herein by reference. A point source typically comprises electrohydraulic apparatus. Fast discharges of electrical energy between tips of closely spaced electrodes give rise to a sequence of spherical waves in a propagating liquid. The electrodes are arranged with respect to an ellipsoidal reflector, which has two focal points. The electrical energy is discharged at the first focus, and the waves are focused onto the second focus.

A planar source typically comprises electromagnetic apparatus. A thin circular membrane applies pressure to the propagation liquid by being jolted or repelled away from a planar coil. Fast discharges of electrical energy into the coil and the associated rapid changes in the magnetic field induce currents in the membrane, turning it into a magnet with a polarization opposite to that of the coil. The ensuing repulsions of the membrane, which is in close contact with the propagating liquid, generate the acoustic waves. U.S. Pat. No. 4,674,505, the disclosure of which is incorporated herein by reference, describes an example of such a planar source with an associated acoustic lens.

Apparatus incorporating a cylindrical source uses an electromagnetic approach similar to that used for the planar source. A coil is mounted on a cylindrical support and a cylindrical membrane, being pushed or repelled radially, gives rise to outwardly propagating cylindrical waves. A parabolic reflector focuses the waves into a point on the cylindrical axis of the system. Cylindrical sources enable using an in-line ultrasonic probe for imaging the focal area. Examples of cylindrical sources are described in U.S. Pat. No. 5,058,569 to Hasssler et al., assigned to Siemens Aktiengesellschaft (Munich, Germany) and U.S. Pat. No. 5,174,280 to Gruenwald et al., assigned to Dornier Mediz-intechnik GmbH (Germering, Germany), the disclosures of which are incorporated herein by reference.

Spherical waves are generated by an array of piezo-electric transducers or by an electromagnetic approach with a spherical membrane being repulsed inwardly into the propagating liquid. No further focusing is required. Spherical sources are mentioned in the background of U.S. Pat. No. 5,174,280.

Each of the prior art acoustic wave generation and focusing apparatus has limitations. Acoustic wave generators generate shocks at a rate of one or two shocks per second, whereas extracorporeal shockwave treatment (ESWT) typically requires thousands of shocks per treatment. The electrohydraulic approach suffers from the disadvantages of non-uniform discharges, pain and high noise level. The electromagnetic planar approach suffers from the disadvantages of high cost and complexity in manufacturing the coil and lens assembly. Acoustic lenses for planar sources are fragile and non-effective for large apertures. In addition to the complexity of manufacturing electromagnetic cylindrical sources, the parabolic reflector is not highly efficient because the source is in the way of reflected waves adjacent thereto. The piezo-electric array is expensive to manufacture, and it is difficult to obtain high-level, well-distributed intensities. The array requires a relatively large aperture that prevents access for x-ray imaging of the focal area.

SUMMARY OF THE INVENTION

The present invention seeks to provide an improved acoustic wave device, wherein acoustic waves generated by the acoustic wave device are focused by a reflector that comprises a curve revolved about the longitudinal axis of the acoustic wave device. The curve may comprise a portion of a conic section having an axis of symmetry angled with respect to the longitudinal axis of the acoustic wave device. For example, a modified parabolic reflector may be arranged with respect to a conical transducer so as to focus acoustic waves emanating therefrom towards a focal point, which is the apex of the conical transducer. As another example, a modified ellipsoidal reflector may be arranged with respect to a ring-shaped transducer so as to focus acoustic waves emanating therefrom towards a focal point, which is one of the foci of the ellipsoid.

Acoustic waves may be generated by an area transducer, such as a truncated conical area transducer. For example, a coil may repel or vibrate a conical membrane to produce acoustic waves. In another example, acoustic waves may be generated by means of a force generator mounted in juxtaposition to the base of the conical transducer. The force generator transmits a force that has two vector components, one vector component generally along the contour of the conical transducer and another vector component generally perpendicularly outwards from the outer contour of the conical transducer. The force component perpendicular to the outer contour generates conical acoustic waves emanating outwards from the outer contour of the conical transducer.

There is thus provided in accordance with a preferred embodiment of the invention an acoustic wave device including an acoustic wave device including a non-cylindrical and non-point acoustic wave transducer adapted to generate an acoustic wave and positioned along a longitudinal axis, and a reflector arranged with respect to the transducer so as to focus an acoustic wave emanating from the transducer to a focal point.

In accordance with a preferred embodiment of the invention the reflector includes a curve revolved about the longitudinal axis.

Further in accordance with a preferred embodiment of the invention the curve includes a portion of a conic section having an axis of symmetry angled with respect to the longitudinal axis. For example, the portion of a conic section may include a parabola or an ellipse.

Still further in accordance with a preferred embodiment of the invention the focal point generally lies on the longitudinal axis.

In accordance with a preferred embodiment of the invention the transducer includes a conical acoustic wave transducer, and the focal point includes an apex of the conical acoustic wave transducer.

Further in accordance with a preferred embodiment of the invention an outer contour of the transducer is angled with respect to an inner contour of the reflector such that an acoustic wave reflected from the inner contour of the reflector is generally not obstructed by the outer contour of the transducer.

In accordance with a preferred embodiment of the invention the transducer includes a ring-shaped acoustic wave transducer, preferably with a center positioned generally at one focus of the ellipse, and wherein the focal point is generally at another focus of the ellipse.

Further in accordance with a preferred embodiment of the invention the acoustic wave device includes a membrane attached to the reflector adapted for an acoustic wave generated by the transducer to propagate therethrough.

Still further in accordance with a preferred embodiment of the invention the acoustic wave transducer includes an open end covered by a membrane.

Additionally in accordance with a preferred embodiment of the invention the acoustic wave transducer includes an open base adapted for an imaging probe to pass therethrough.

In accordance with a preferred embodiment of the invention an electrical element is disposed on an outer contour of the transducer, the electrical element being areally configured on the outer contour for radiating acoustic waves outwardly from the outer contour.

Further in accordance with a preferred embodiment of the invention a force generator is mounted in juxtaposition to a base of the transducer, the force generator being adapted to transmit a force to an outer contour of the transducer, which force gives rise to an acoustic wave.

Still further in accordance with a preferred embodiment of the invention the force has a vector component generally perpendicular to the outer contour of the transducer that generates acoustic waves emanating outwards from the outer contour of the transducer.

The force generator may include at least one of a reciprocating hammer device, a "flying" mass accelerator adapted to cause a mass to impinge on the transducer, an explosive, an underwater electrical discharge unit, an electromagnetic actuator, a piezoelectric actuator, a pneumatic actuator and a hydraulic actuator.

BRIEF DESCRIPTION OF THE DRAWINGS

The present invention will be understood and appreciated more fully from the following detailed description taken in conjunction with the drawings in which.

DETAILED DESCRIPTION OF A PREFERRED EMBODIMENT

Figure 1:
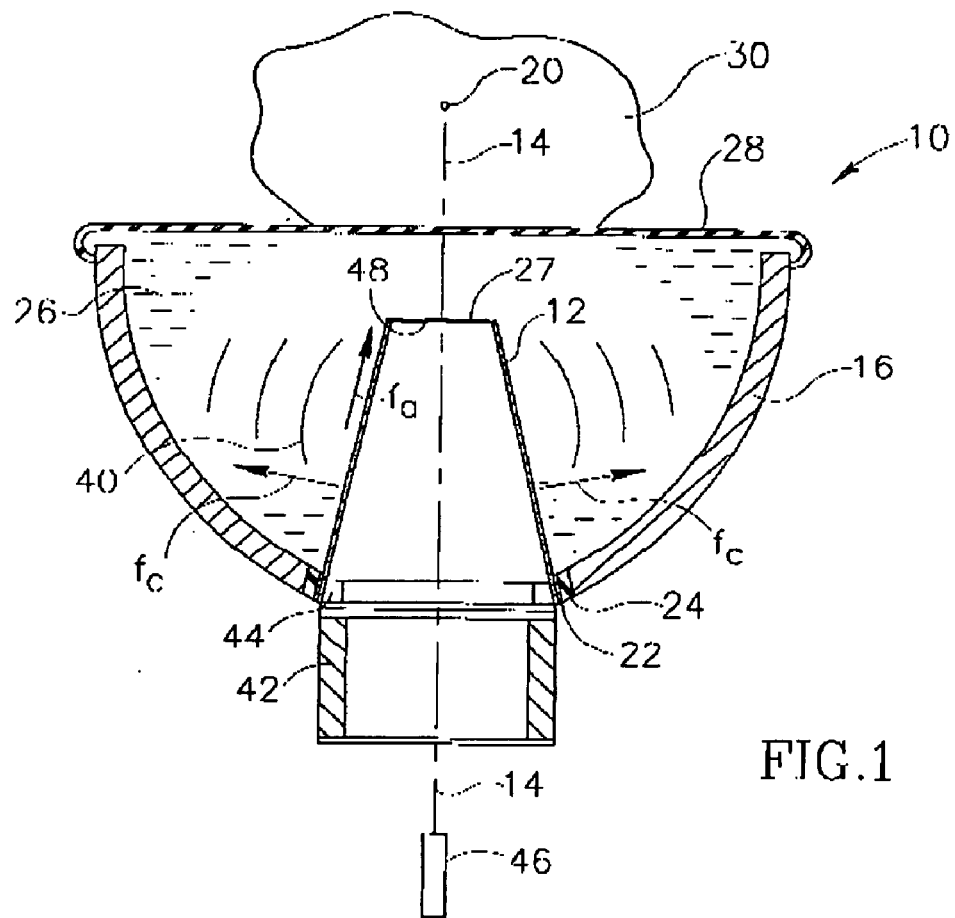
FIG. 1 is a simplified pictorial illustration of an acoustic wave device, constructed and operative in accordance with a preferred embodiment of the invention, with a non-cylindrical (e.g., cone-shaped) acoustic wave transducer and a modified parabolic reflector.

Reference is now made to FIG. 1 which illustrates an acoustic wave device 10, constructed and operative in accordance with a preferred embodiment of the present invention.

Figure 2:
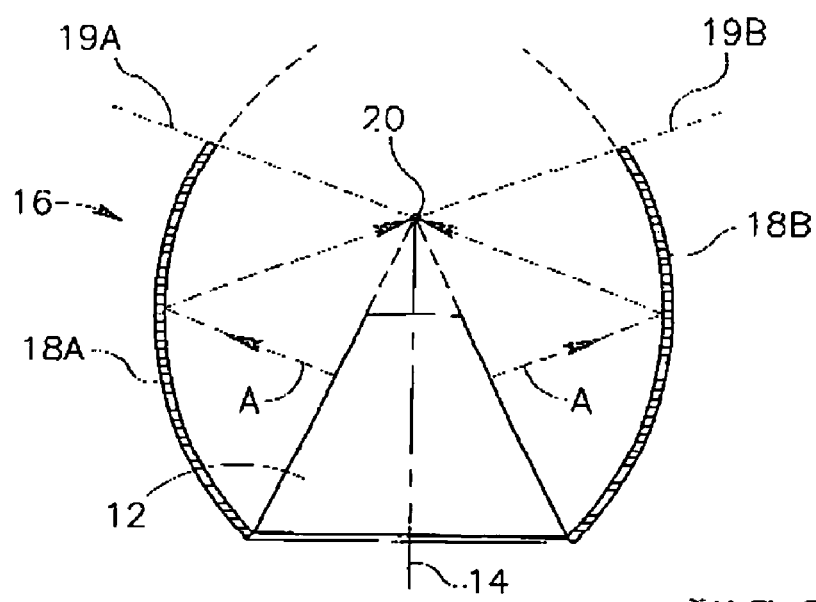
FIG. 2 is a simplified geometrical diagram of the acoustic wave device of FIG. 1.

In the embodiment of FIG. 1, acoustic wave device 10 includes a non-cylindrical and non-point acoustic wave transducer 12. For example, acoustic wave device 10 may be shaped like a cone, most preferably a truncated cone, with a longitudinal axis (its axis of symmetry) 14. A modified parabolic reflector comprising an at least partially parabolic reflector 16 is arranged with respect to transducer 12 so as to focus an acoustic wave emanating from transducer 12. A preferred arrangement of reflector 16 with respect to transducer 12 is described now with reference to FIG. 2.

As is well known, from the definition of a parabolic surface, any ray emanating from a focal point 20 of a parabola that impinges upon the parabola is reflected from the parabola parallel to an axis of symmetry of the parabola (i.e., its axis of revolution). The converse is also true: any ray A parallel to the axis of symmetry of the parabola, which impinges upon the parabola, is reflected to focal point 20. The contour of cone-shaped transducer 12 may thus be arranged such that rays that propagate perpendicularly away from the cone contour are parallel to the axis of symmetry of the parabola. Reflector 16 may be accordingly constructed of two portions of parabolas revolved symmetrically about the longitudinal axis 14 of cone-shaped transducer 12, one portion 18A (half of a parabola) with its axis of symmetry 19A and another portion 18B (half of a parabola) with its axis of symmetry 19B. Thus, reflector 16 circumscribes transducer 12 so that outwardly radiated acoustic waves from transducer 12 are reflected by reflector 16 towards focal point 20, situated at the cone apex on axis 14. Transducer 12 may fit through an aperture 22 formed in reflector 16, and may be sealed thereat by a sealing ring 24 (FIG. 1).

The inner volume of reflector 16 may be filled with a propagation liquid 26, and an open end 48 of transducer 12 may be covered with a membrane 27 in order to seal the inside of the conical transducer 12 from ingress therein of propagation liquid 26. The end face of reflector 16 may be covered with another membrane 28. Acoustic wave device 10 may be placed against or near a target 30, which it is desired to treat. Acoustic waves generated by transducer 12 may propagate towards focal point 20, located in target 30, via propagating liquid 26 and through membrane 28. The acoustic waves may be produced in a variety of manners, as is described hereinbelow with reference to FIGS. 1 and 4.

One of the advantages of the conical shaped transducer 12 over a cylindrical transducer of the prior art is in significantly reduced blockage of the reflected acoustic waves.

Specifically, the outer contour of transducer 12 may be angled with respect to the inner contour of reflector 16 such that an acoustic wave reflected from the inner contour of reflector 16 is generally not obstructed by the outer contour of transducer 12.

Figure 3:
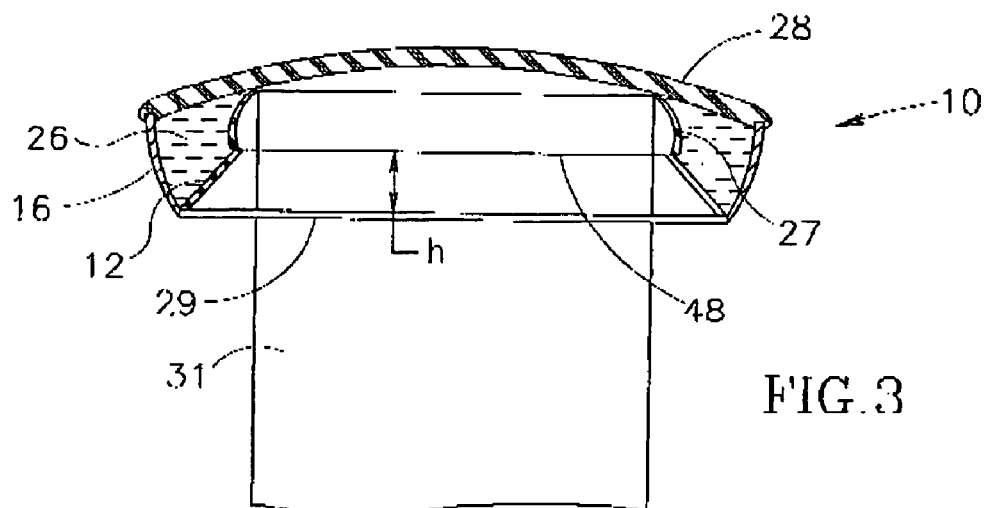
FIG. 3 is a simplified illustration of the acoustic wave device of FIG. 1, with a wide opening for an imaging probe to pass into or through the acoustic wave transducer, in accordance with a preferred embodiment of the invention.

Reference is now made to FIG. 3, which illustrates another advantage of the acoustic wave device 10 over the prior art. In the prior art, which uses a cylindrical acoustic wave transducer, the opening of the cylinder must be small to minimize the blockage of the reflected acoustic waves. This means that the prior art is limited in the size and type of probes that may be introduced through the cylinder. In particular, imaging probes, such as but not limited to X-ray probes, which typically have a diameter of 8–10 cm, cannot be introduced through the cylinder. Since the present invention does not suffer from the disadvantage of blockage of reflected acoustic waves, conical transducer 12 may be configured with a wide open base 29 for an imaging probe 31 to pass into or through the cone. (Imaging probe 31 may also be employed without passing into or through the cone, if desired.) It is seen that membranes 27 and 28 may be flexible (e.g., constructed from an elastomer, such as but not limited to, latex, silicone, polyurethane and the like), so that probe 31 may press membrane 27 against membrane 28, and both membranes against the patient (not shown). The height h of the cone may be narrow, if desired, and yet maintain a large area for an area transducer to produce acoustic waves from the contour of the cone.

Figure 4:
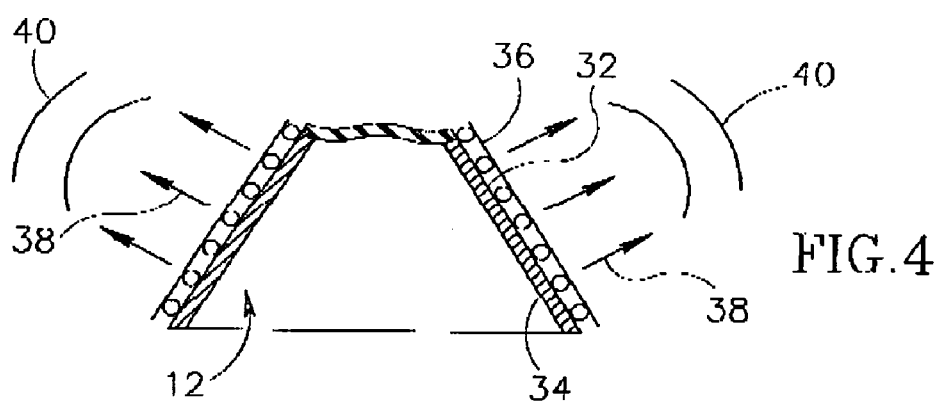
FIG. 4 is a simplified sectional illustration of a truncated conical area transducer that may be used to generate acoustic waves, with a coil and membrane arrangement, in accordance with a preferred embodiment of the invention.

Reference is now made to FIG. 4, which illustrates a truncated conical area transducer that may be used to generate the acoustic waves, in accordance with a preferred embodiment of the invention. The area transducer comprises an electrical element 32, such as a coil, mounted on a truncated conical support 34 of transducer 12. A membrane 36 is shaped to conform to the conical outer contour of support 34 and is disposed on electrical element 32. The coil is adapted to move (e.g., repel or vibrate) membrane 36 outwards from truncated conical support 34, generally in the direction of arrows 38, so as to propagate acoustic waves 40 in a direction outwards from the contour of transducer 12. As mentioned hereinabove, acoustic waves 40 reflect off reflector 16 and propagate towards focal point 20 through membrane 28 (FIG. 1).

It is appreciated that such a coil and membrane arrangement is just one example of an area transducer. The skilled artisan will appreciate that any area transducer that converts non-mechanical energy into acoustic waves at the interface with propagating liquid 26 may be used in the present invention for generating acoustic waves 40, such as the types of area transducers described in U.S. Pat. Nos. 5,058,569 and 5,174,280.

Reference is now made again to FIG. 1. Another way of generating acoustic waves in the present invention is by means of a force generator 42 mounted in juxtaposition to the base of conical transducer 12. Force generator 42 may be coupled to transducer 12 by means of a mechanical coupler 44. Force generator 42 is adapted to transmit a force generally along axis 14, which force is transmitted to the outer contour of transducer 12, thereby giving rise to acoustic waves 40. Specifically, the force has two vector components, one vector component $f_a$ generally along the contour of conical transducer 12 and another vector component $f_c$ generally perpendicularly outwards from the outer contour of transducer 12. The force component $f_c$ generates conical acoustic waves 40 emanating outwards from the outer contour of transducer 12, as seen in FIG. 1. The direction of the force $f_a$ (towards the cone apex or away from it) determines the polarity of the acoustic waves 40 (expanding or retracting). The intensity of the waves is proportional to the sine of the cone angle.

The force generator 42 may be any suitable device for generating force impulses, such as, but not limited to, a reciprocating hammer device, a "flying" mass accelerator adapted to cause a mass to impinge on transducer 12, an explosive, an underwater electrical discharge unit, an electromagnetic actuator, a piezoelectric actuator, a pneumatic actuator or a hydraulic actuator, for example.

Transducer 12 is preferably hollow so that imaging apparatus 46, such as an in-line ultrasonic probe, may be used to image the focal area, such as via the open truncated end 48 of transducer 12.

As described hereinabove, the acoustic wave devices of the present invention cooperate with a reflector that comprises a curve revolved about the longitudinal axis of the acoustic wave device. The curve may comprise a portion of a conic section (e.g., portions 18A and 18B of FIG. 2) having an axis of symmetry (e.g., axes 19A and 19B of FIG. 2) angled with respect to the longitudinal axis (e.g., axis 14 of FIG. 2). Other curves may be used as well to carry out the invention. A further example is described with reference to FIG. 5.

Figure 5:
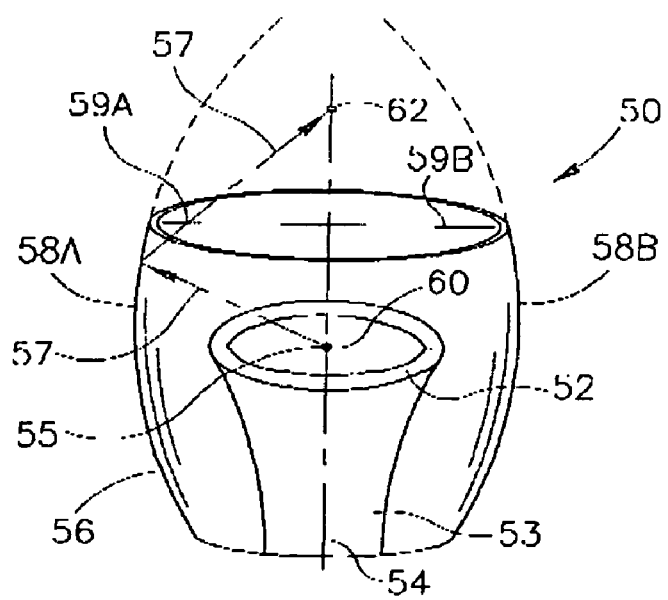
FIG. 5 is a simplified pictorial illustration of an acoustic wave device, constructed and operative in accordance with another preferred embodiment of the invention, with a ring-shaped acoustic wave transducer and a modified ellipsoidal reflector.

Reference is now made to FIG. 5 which illustrates an acoustic wave device 50, constructed and operative in accordance with another preferred embodiment of the present invention. In the embodiment of FIG. 5, acoustic wave device 50 includes a ring-shaped acoustic wave transducer 52 adapted to generate acoustic waves. The ring-shaped acoustic wave transducer 52 may include one or more of a variety of acoustic wave transducers, such as but not limited to, an array of a plurality of point sources positioned around a ring, a thin circular membrane ring that applies pressure to the propagation liquid by being jolted or repelled away from a coil, or an array of piezo-electric transducers positioned around the ring. The ring-shaped acoustic wave transducer 52 may be supported by any suitable support structure 53.

The ring-shaped acoustic wave transducer 52 has a longitudinal axis (its axis of symmetry) 54 that passes through a center 55 of the transducer 52. A modified ellipsoidal reflector 56 is arranged with respect to transducer 52 so as to focus an acoustic wave emanating from transducer 52. Reflector 56 may be constructed of two portions revolved symmetrically about the longitudinal axis 54 of ring-shaped transducer 52, one portion 58A (half of an ellipse) with its axis of symmetry 59A and another portion 58B (half of a parabola) with its axis of symmetry 59B. Axes of symmetry 59A and 59B may be collinear. The ring-shaped acoustic wave transducer 52 is preferably positioned with its center 55 generally at one focus 60 of either ellipse, and reflector 56 focuses acoustic waves 57 emanating from transducer 52 to a focal point 62, which is generally at the other focus of either ellipse.

The rest of the construction of acoustic wave device 50 is preferably similar to that of acoustic wave device 10 (with propagation liquid 26, etc.).

The ring-shaped acoustic wave transducer 52 generates acoustic waves 57 generally omnidirectionally towards the reflecting surfaces of reflector 56, and these waves 57 are focused to focal point 62 by virtue of the elliptical geometry of the reflecting surfaces.

It will be appreciated by person skilled in the art, that the present invention is not limited by what has been particularly shown and described herein above. Rather the scope of the present invention is defined only by the claims that follow.

What is claimed is:

1. An acoustic wave device comprising:
a truncated conical acoustic wave transducer adapted to generate an acoustic wave and positioned along a longitudinal axis; and
a reflector arranged with respect to said transducer so as to focus an acoustic wave emanating from said transducer to a focal point, said reflector comprising a first curve and a second curve revolved about said longitudinal axis,
wherein said first curve comprises a portion of a first conic section having an axis of symmetry angled at a first non-zero, non-perpendicular angle with respect to said longitudinal axis, and said second curve comprises a portion of a second conic section having an axis of symmetry angled at a second non-zero, non-perpendicular angle with respect to said longitudinal axis, and
a membrane attached to said reflector adapted for an acoustic wave generated by said transducer to propagate therethrough.

2. The acoustic wave device according to claim 1, wherein said first and second conic sections each comprises a parabola.

3. The acoustic wave device according to claim 1 wherein said first and second conic sections each comprises an ellipse.

4. The acoustic wave device according to claim 1 wherein said focal point generally lies on said longitudinal axis.

5. The acoustic wave device according to claim 1 wherein said acoustic wave transducer comprises an open base of sufficient size for an imaging probe to pass therethrough.

6. The acoustic wave device according to claim 1 and further comprising a force generator mounted in juxtaposition to a base of said transducer, said force generator being adapted to transmit a force to an outer contour of said transducer, which force gives rise to an acoustic wave.

7. The acoustic wave device according to claim 6 wherein said force has a vector component generally perpendicular to said outer contour of said transducer that generates acoustic waves emanating outwards from said outer contour of said transducer.

8. The acoustic wave device according to claim 6 wherein said force generator comprises at least one of a reciprocating hammer device, a "flying" mass accelerator adapted to cause a mass to impinge on said transducer, an explosive, an underwater electrical discharge unit, an electromagnetic actuator, a piezoelectric actuator, a pneumatic actuator and a hydraulic actuator.

* * * * *